United States Patent [19]

Koshar

[11] Patent Number: 4,600,774

[45] Date of Patent: Jul. 15, 1986

[54] CYCLIC SULFOPERFLUOROALIPHATICCARBOXYLIC ACID ANHYDRIDES AND AMIDE DERIVATIVES THEREOF

[75] Inventor: Robert J. Koshar, Mahtomedi

[73] Assignee: Minnesota Mining and Manufacturing Company, St. Paul, Minn.

[21] Appl. No.: 744,493

[22] Filed: Jun. 13, 1985

Related U.S. Application Data

[62] Division of Ser. No. 326,761, Dec. 2, 1981, abandoned, which is a division of Ser. No. 229,872, Jan. 30, 1981, Pat. No. 4,332,954.

[51] Int. Cl.$^4$ .................. C07C 143/13; C07C 143/74; C07D 265/28
[52] U.S. Cl. .................................. 544/85; 260/501.12; 260/501.16; 260/501.21; 260/503; 260/507 R; 260/513 F; 546/189; 546/190; 548/146; 548/200; 548/215; 548/540; 548/542; 560/10; 560/12; 560/121; 560/122; 560/123; 560/125; 560/149; 560/151
[58] Field of Search .................. 560/10, 12, 121, 122, 560/123, 125, 149, 151; 260/501.12, 501.16, 501.21, 503, 507 R, 513 F; 544/85; 546/189, 190; 548/146, 200, 215, 540, 542

[56] References Cited

U.S. PATENT DOCUMENTS

| | | | |
|---|---|---|---|
| 2,732,398 | 1/1956 | Brice et al. | 260/503 |
| 2,809,990 | 10/1957 | Brown | 560/149 |
| 2,852,554 | 9/1958 | England | 560/149 |
| 3,347,676 | 10/1967 | Cripps | 96/115 |
| 3,796,724 | 3/1974 | Scheidl | 549/33 |
| 3,842,019 | 10/1974 | Kropp | 260/2 EP |
| 4,244,886 | 1/1981 | Caporiccio et al. | 260/513 F |

FOREIGN PATENT DOCUMENTS

| | | |
|---|---|---|
| 1281441 | 10/1968 | Fed. Rep. of Germany. |
| 2420480 | 11/1975 | Fed. Rep. of Germany. |
| 2124173 | 11/1977 | Fed. Rep. of Germany. |
| 1120304 | 7/1968 | United Kingdom. |
| 2051831 | 1/1981 | United Kingdom. |
| 2053902 | 2/1981 | United Kingdom. |

OTHER PUBLICATIONS

Howells et al., Chemical Reviews, 77, 69–92 (1977).
T. R. Forbus et al., *J. Org. Chem.*, 44, 313, (1979).
Alm, *Modern Paint and Coatings*, Oct. 1980, pp. 88–92.
Breslow et al., *Heterocyclic Compounds–Multi–Sulfur and Sulfur and Oxygen Five and Six Membered Heterocyclics*, Interscience Publishers (New York), 1966, Part One, pp. 95 and 96, Part Two, p. 774.

*Primary Examiner*—Richard L. Raymond
*Attorney, Agent, or Firm*—Donald M. Sell; James A. Smith; David R. Cleveland

[57] ABSTRACT

Cyclic sulfoperfluoroaliphaticcarboxylic acid anhydrides, amide derivatives thereof, a process for making the same, curable compositions containing cyclic sulfoperfluoroaliphaticcarboxylic acid anhydrides or amide derivatives thereof and cationically-sensitive monomers, and a process for using cyclic sulfoperfluoroaliphaticcarboxylic acid anhydrides or amide derivatives thereof as catalysts for the cure of cationically-sensitive monomers.

4 Claims, No Drawings

CYCLIC SULFOPERFLUOROALIPHATICCARBOXYLIC ACID ANHYDRIDES AND AMIDE DERIVATIVES THEREOF

This is a division of application Ser. No. 326,761, filed Dec. 2, 1981, and now abandoned, which is in turn a division of application Ser. No. 229,872, filed Jan. 30, 1981, now U.S. Pat. No. 4,332,954.

TECHNICAL FIELD

This invention relates to cyclic fluorocarbon anhydrides, amide derivatives thereof, and a process for their synthesis. In another aspect, this invention relates to curable compositions containing cationically-sensitive monomers, such as epoxides, and said cyclic fluorocarbon anhydrides or amide derivatives thereof. In yet another aspect, this invention relates to a process for curing cationically-sensitive monomers, utilizing as catalyst said cyclic fluorocarbon anhydrides or amide derivatives thereof.

BACKGROUND ART

Processes of polymerizing and curing cationically-sensitive monomers such as cyclic ethers (e.g., epoxides), vinyl ethers, and N-vinyl compounds, in the presence of catalysts, specifically Lewis acids, such as boron trifluoride, aluminum chloride, and the like, are well known. However, many of these catalysts are highly corrosive to various substrates such as metals. Other known catalysts for the polymerization and curing of cationically-sensitive monomers are undesirably toxic. Further, many of these catalysts rapidly catalyze the polymerization of the monomers with which they are admixed and cannot be used where a definite or prolonged shelf life and/or pot life is desired or required. Though some of these prior art catalysts can be used in a latent form, e.g., $BF_3 \cdot NH_2C_2H_5$, their latency is affected by moisture and prolonged latency is difficult to achieve; in addition, when these latent catalysts are activated, this gives rise to the aforementioned objectionable corrosiveness. Also, many known catalysts are not effective for polymerization of a broad range of cationically-sensitive monomers, e.g., for polymerization of both epoxides and cyclic siloxanes.

Various linear perfluoroaliphaticsulfonic acid anhydrides of the formula $(RSO_2)_2O$, where R is perfluoroalkyl, are described in U.S. Pat. No. 2,732,398. U.K. Patent specification No. 1,120,304 discloses the use of the anhydride of trifluoromethanesulfonic acid as a catalyst for use in the polymerization of various cationically-sensitive monomers.

The utility of linear fluorocarbonsulfonic acid anhydrides (e.g., those derived from monofunctional perfluoroaliphaticsulfonic acids) as perfluoroaliphaticsulfonylation or acylation agents is also known. Use of the anhydride $(CF_3SO_2)_2O$ as a trifluoromethanesulfonylation agent for formation of trifluoromethanesulfonamides by reaction with ammonia or amines is disclosed in Chemical Reviews, 77, 69–92 (1977). T. R. Forbus and J. C. Martin, J. Org. Chem., 44, 313 (1979) have disclosed the preparation of the mixed anhydride, $CF_3SO_2OC(O)CF_3$, and its use as a trifluoroacetylation reagent for aromatic compounds. In these reactions, however, the above linear anhydrides produce not only the desired trifluoromethanesulfonylation or acylation product but also produce an equivalent amount of trifluoromethanesulfonic acid or salt thereof as by-product. For example, the reaction of $(CF_3SO_2)_2O$ with ammonia provides equal portions of trifluoromethanesulfonamide and the ammonium salt of trifluoromethanesulfonic acid as a by-product. Such by-product is undesirable because of unfavorable economics in the preparation of the desired product.

Cyclic fluorocarbon acid anhydrides are highly desirable compositions since, in contrast to the above linear anhydrides, reaction of cyclic anhydrides with reagents such as ammonia or amines can produce useful difunctional products by ring-opening reactions without formation of the above-described by-products. Very few such cyclic anhydrides are known, however, because of many factors such as ring instability, or decomposition, e.g., decarboxylation, during the process of ring formation, or because of the inability of many difunctional acids to undergo ring closure by dehydration. Cyclic anhydrides such as perfluorosuccinic acid anhydride are well known and provide useful products by ring-opening reactions such as reaction with ammonia to produce ammonium salts of the perfluorocarboxylic acids containing terminal carboxamide $(CONH_2)$ functional groups. However, such cyclic anhydrides or their amide derivative(s) do not exhibit the catalytic properties of the cyclic anhydrides or amide derivatives of the invention described below.

The use of ammonia or amine salts of monofunctional perfluoroaliphaticsulfonic acids as latent catalysts for the polymerization of cationically-sensitive monomers is well known, see U.S. Pat. No. 3,842,019 and R. R. Alm, Modern Paint and Coatings, October, 1980, pages 88–92. However, the salts described in these references do not include a second functional group in the molecule (e.g., a carboxamido group) as found in the ammonium or organo-ammonium salts of this invention.

DISCLOSURE OF INVENTION

The present invention provides, the one aspect, cyclic anhydrides of omega-sulfoperfluoroaliphaticcarboxylic acids, having the formula:

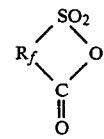

wherein $R_f$ is perfluoroalkylene having 2 to 5 backbone or catenary carbon atoms or perfluorocycloalkylene having 4 to 7, preferably 6, ring atoms, $R_f$ optionally being substituted by one or more, e.g., one to three, straight, branched, or cyclic perfluoroalkyl groups of 1 to 12, and preferably 1 to 4 carbon atoms, with $R_f$ having a total of up to 14 carbon atoms. Preferably $R_f$ has the formula $-CF_2-_m$ where m is 2 to 4.

The present invention also provides a process for the preparation by ring formation of said cyclic anhydrides of omega-sulfoperfluoroaliphaticcarboxylic acids comprising the steps of:
(a) mixing omega-sulfoperfluoroaliphaticcarboxylic acid precursor with excess phosphorus pentoxide,
(b) heating the resulting mixture to dehydrate and cyclize said omega-sulfoperfluoroaliphaticcarboxylic acid under anhydrous conditions, and
(c) recovering said cyclic anhydride under anhydrous conditions from the resulting reacted mixture.

The invention further provides carboxamide and sulfonamide derivatives of said cyclic anhydrides, which carboxamides and sulfonamides are useful as latent catalysts for the polymerization of cationically-sensitive monomers. Said carboxamides and sulfonamides are prepared by reacting one or more of said cyclic anhydrides of omega-sulfoperfluoroaliphaticcarboxylic acids with one or more protonic nitrogenous base having a $pk_b$ of less than about 13.2. The preferred amide catalysts comprise carboxamides, sulfonamides, and mixtures thereof having the formulae:

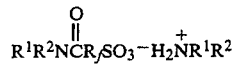     II

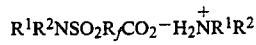     III wherein:

$R_f$ is as defined above;

each $R^1$ and $R^2$ is independently hydrogen, or a monovalent organic radical (preferably alkyl, alkyloxy, alkenyl, cycloalkyl, aryl or aryloxy, having 1 to 10 carbon atoms) which can be the same as or different from any other $R^1$ or $R^2$, or each $R^1$ and $R^2$ bonded to the same N atom can combine with one another to form a cyclic structure containing the N atom, and $R^1$ and $R^2$ can contain from 1 to about 20 carbon atoms, can be straight chain, branched or cyclic, can be saturated, unsaturated or aromatic, can contain skeletal or catenary hetero atoms, i.e., atoms other than carbon (e.g., oxygen or sulfur), and can be unsubstituted or substituted with non-interfering moieties, i.e., moieties which do not interfere with the functioning of said amides as latent acid catalysts. Compounds of formula II above are especially preferred.

This invention also provides curable compositions comprising cationically-sensitive monomers and a catalytically effective amount of said cyclic anhydrides of omega-sulfoperfluoroaliphaticcarboxylic acids or said carboxamide or sulfonamide derivatives thereof.

This invention also provides a process for the polymerization of cationically-sensitive monomers, comprising the steps of:

(a) mixing with said monomers a catalytically effective amount of said cyclic anhydride of omega-sulfoperfluoroaliphaticcarboxylic acid or said carboxamide or sulfonamide derivative thereof, thereby forming a mixture, and (b) allowing said mixture to polymerize, or heating said mixture to effect polymerization thereof.

DETAILED DESCRIPTION

In the practice of the present invention, said cyclic anhydrides of omega-sulfoperfluoroaliphaticcarboxylic acids (hereinafter, for brevity, also designated as cyclic anhydrides) are preferably prepared by the dehydration and cyclization of the precursor hydrated omega-sulfoperfluoroaliphaticcarboxylic acids (IV, below), caused by heating the precursor acid in the presence of an excess of a suitable dehydrating agent, e.g., phosphorus pentoxide, as shown in Equation 1 below, at a temperature sufficient to provide efficient and controllable reaction between the precursor acid and phosphorus pentoxide. Such temperature is preferably about 100° C. to 300° C. and most preferably is about 150° C. to 250° C.

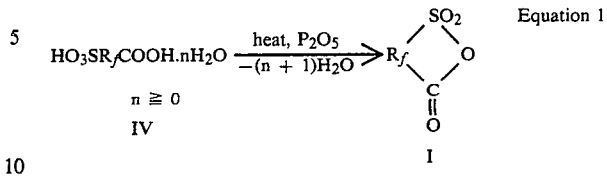

The resulting cyclic anhydride product is volatile and can be collected by distillation. The cyclic anhydride is prepared and stored under anhydrous conditions.

The amount of phosphorus pentoxide can vary depending on the amount of water of hydration present in the precursor omega-sulfoperfluoroaliphaticcarboxylic acid hydrate. Generally, a one mole excess of phosphorus pentoxide is used with anhydrous precursor acid, but greater amounts such as up to a ten mole excess or more can be used with hydrates of the precursor acid.

An inert diluent such as sand, glass beads, or a high boiling fluorinated organic liquid is usually employed in the dehydration and cyclization reaction. The use of inert, fluorinated organic liquid diluent having a boiling point which is substantially higher (e.g., 50° C.) than the boiling point of the desired cyclic anhydride product is preferred since such a diluent facilitates intimate contact of the reactants, efficient stirring, and good heat transfer, thus aiding in the rapid completion of the dehydration and cyclization reaction.

When fluorinated diluent is used, the volatile cyclic anhydride products can be isolated most conveniently on a small scale by purging the heated reaction flask with nitrogen gas and condensing the anhydride in a receiver cooled with "Dry Ice" to −78° C. Alternatively, the reaction mixture can be subjected to distillation.

The crude cyclic anhydride, obtained by any of the above procedures, can be additionally purified by redistillation, or can be used directly as an intermediate in the preparation of said carboxamide and sulfonamide derivatives. Said carboxamide and sulfonamide derivatives will sometimes be collectively referred to hereafter as "amide derivatives". The cyclic anhydride should be stored in a sealed dry vessel to avoid hydrolysis through contact with water or water vapor until it is needed for use as a catalyst or for the preparation of amide derivatives. The presence of water or water vapor can cause the cyclic anhydride to hydrolyze and form the precursor linear acid hydrate.

The omega-sulfoperfluoroaliphaticcarboxylic acid precursors for the preparation of the cyclic anhydrides of this invention can be obtained by means of a series of reactions, starting with the conversion of hydrocarbon sultones or hydrocarbon omega-fluorosulfonylaliphaticacyl fluorides to the corresponding omega-fluorosulfonylperfluoroaliphaticacyl fluorides, $FSO_2R_fCOF$, by electrochemical fluorination in anhydrous hydrogen fluoride in accordance with the procedure described in U.S. Pat. No. 2,732,398. Alkaline hydrolysis of said omega-fluorosulfonylperfluoroaliphaticacyl fluoride is usually performed using aqueous alkali metal hydroxide such as sodium or potassium hydroxide. A convenient method for preparation of the sodium salt involves the gradual addition of said omega-fluorosulfonylperfluoroaliphaticacyl fluoride to a stirred aqueous alcoholic solution (e.g., 80 to 85% by volume methanol) at room temperature, followed by neutralization with aqueous sodium hydroxide. The resulting neutralized mixture is filtered to remove insoluble sodium fluoride and the filtrate evaporated yielding the salt, Na-SO$_3$R$_f$COONa, which is further dried by heating to 100° C.

The recovered metal salt, MSO$_3$R$_f$COOM (where M is, for example, Na or K), is dissolved in water, and the resulting solution is placed on a column of cationic ion-exchange resin in the acid form (e.g., "Amberlite IR-120," commercially available from Rohm & Haas, Inc.). The column is eluted with distilled or deionized water, and the eluate is concentrated under reduced pressure at about 50° C. to constant weight to yield the desired acid hydrate precursor for the preparation of said cyclic anhydrides of Formula I, above.

Representative cyclic omega-sulfoperfluoroaliphatic-carboxylic acid anhydrides of this invention include the following compounds:

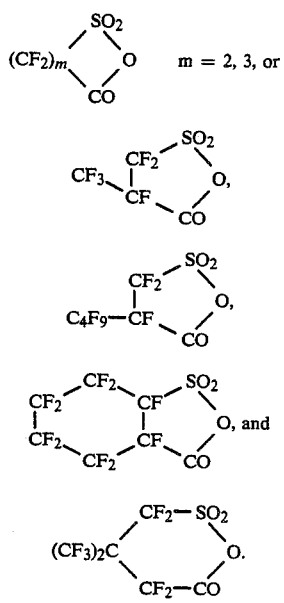

The amide derivatives of the cyclic anhydrides of the invention are obtained by reaction of the cyclic anhydride with a stoichiometric or excess amount of protonic nitrogenous base having a pk$_b$ less than about 13.2, such as ammonia, hydrazines, and organic amines containing at least one reactive hydrogen atom attached to nitrogen. The term "hydrazine" as used herein broadly includes hydrazine and hydrazine derivatives in which one or more hydrogen atoms bonded to nitrogen is replaced with R$^1$ or R$^2$ organic groups. Preferred nitrogenous bases have the formula HNR$^1$R$^2$, where R$^1$ and R$^2$ are as defined above. The cyclic anhydrides of this invention are reactive even with weakly basic amines such as diphenylamine (which has a pk$_b$ of 13.12).

The reaction of the cyclic anhydride with the protonic nitrogenous base is carried out at a temperature which provides efficient and controlled reaction between the cyclic anhydride and nitrogenous base. Such temperature is generally about −30° to 150° C., depending on the reactivity of the nitrogenous base. The reaction usually occurs readily at room temperature, with cooling sometimes being desirable to control the exotherm. The reactants can be combined in any order but a preferred method of conducting the amide formation reaction is by the slow addition of ammonia or amine to a stirred, cold (e.g., 0° to 10° C.) solution of the cyclic anhydride in an anhydrous inert solvent such as methylene chloride. Other suitable inert solvents include diethyl ether, isopropyl ether and acetonitrile. The amide derivative is a salt in the form of an oil, grease, or solid. The oily or greasy salts are purified by decanting or evaporation of solvent. The solid salts can be isolated by filtration and purified by crystallization from an appropriate solvent or solvent mixture.

Preferred amide derivatives are obtained by the reaction of the cyclic anhydride with ammonia or a primary or secondary organic amine. The major product formed is represented by Formula II above and is referred to hereinafter as the carboxamidoperfluoroaliphaticsulfonate. The minor product formed is represented by Formula III above and is referred to hereinafter as the sulfonamidoperfluoroaliphaticcarboxylate. Generally only small amounts of minor product are obtained. However, when the protonic nitrogenous base used in the preparation of amide derivatives is ammonia, then a 1:1 mixture of compounds of Formulas II and III above is generally obtained.

Representative organic radicals R$^1$ and R$^2$ include methyl, ethyl, butyl, dodecyl, octadecyl, phenyl, o-tolyl, cyclopentyl, cyclohexyl, isopropyl, 2-ethylhexyl, propenyl, 2-butenyl, methoxymethyl, methoxyethyl, ethoxyethyl, ethoxybutyl, 4-methoxyphenyl, and eththioethyl. R$^1$ and R$^2$ together with N can be, for example, N-piperidyl or N-pyrrolidyl.

Representative organic amines having a pk$_b$ of about 13.2 or less and the formula HNR$^1$R$^2$ are described in "Handbook of Chemistry and Physics", 47th Edition, D-85 (1966-1967). Examples include methylamine, n-butylamine, n-octylamine, isobutylamine, cyclohexylamine, diethylamine, dioctylamine, diisobutylamine, diallylamine, glycine and its ethyl ester, aniline, N-methylaniline, p-chloroaniline, p-cyanoaniline, o-toluidine, m-aminophenol, diphenylamine, alpha-naphthylamine, morpholine, oxazolidine, thiazolidine, p-methoxyaniline, and the like. Such amines can contain substituent groups which are essentially non-reactive or less reactive than the amino group of the organic amine, including halogen, hydroxy, alkoxy, nitrile, carboxy and carboalkoxy.

Other protonic nitrogenous bases containing more than one basic —NH— or —NH$_2$— group can afford amide derivatives of this invention which are useful as catalysts. Such derivatives are generally more complex than the products represented by Formulae II and III and can be oligomers or polymers. Such nitrogenous bases include hydrazine, sym-dimethylhydrazine, methylhydrazine, methylhydrazinecarboxylate, guanidine, aminoguanidine, diethylenetriamine, triethylenetetramine, hexamethylenediamine, piperazine, polyethyleneimine, and the like.

Representative simple (i.e., non-oligomeric) amide derivatives of the cyclic anhydrides of this invention include the following:

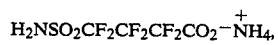

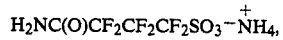

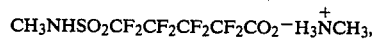

-continued

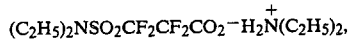

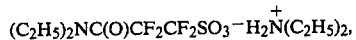

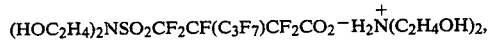

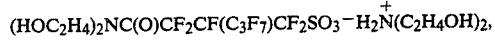

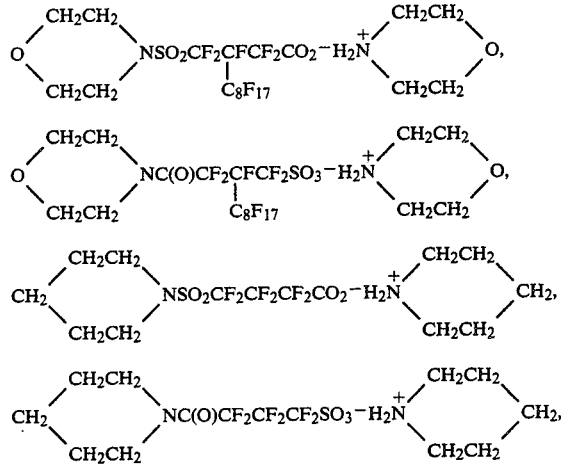

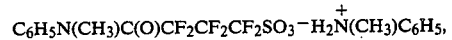

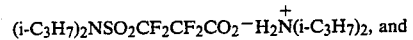

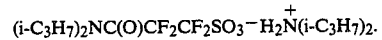

The cyclic anhydrides of this invention and amide derivatives thereof (sometimes collectively referred to hereafter as the compounds of the invention) are useful for the polymerization or curing of cationically-sensitive monomers. The term "monomers" as used herein includes not only low molecular weight cationically-sensitive materials, but also high molecular weight polymeric compositions, e.g., resins containing one or more cationically-sensitive polymerizable groups of the types described below, which in the presence of the compounds of this invention will undergo polymerization or crosslinking.

Said amide derivatives of the cyclic anhydrides of this invention are latent catalysts, particularly with respect to epoxides. The term "latent catalyst" as used herein means a catalyst which does not exhibit or manifest any substantial curing or catalytic effect on monomer admixed therewith during normal storage or handling of such mixtures until the mixture is subjected to heat for the purpose of activation, though some small or otherwise tolerable or insignificant curing of the monomer may take place before activation, as evidenced by a slight increase in viscosity. Similarly, a composition which has latency or is characterized as being latently curable is one which during the period prior to being heated to effect cure, exhibits little if any gelling, polymerization, etc., though some small or otherwise tolerable or insignificant curing may take place during such period.

The monomers that can be cured or polymerized with the compounds of this invention, using the latter in a catalytically effective amount, are those known to undergo cationic polymerization and include 1,2-, 1,3-, and 1,4-cyclic ethers (also designated as 1,2-, 1,3-, and 1,4-epoxides), vinyl ethers, N-vinyl compounds, ethylenically unsaturated hydrocarbons, cyclic formals, and cyclic organosiloxanes. An extensive list of cationically polymerizable monomers which can be used in this invention is given in U.S. Pat. Nos. 3,347,676 and 3,842,019.

The cyclic ethers which can be polymerized in accordance with this invention include those described in "Ring-Opening Polymerizations," Vol. 2, by Frisch and Reegan, Marcel Dekker, Inc. (1969). Suitable 1,2-cyclic ethers are the monomeric and polymeric types of epoxides. They can be aliphatic, cycloaliphatic, aromatic, or heterocyclic and will typically have an epoxy equivalency of from 1 to 6, preferably 1 to 3. Particularly useful are the aliphatic, cycloaliphatic, and glycidyl ether type 1,2-epoxides such as propylene oxide, epichlorohydrin, styrene oxide, vinylcyclohexene oxide, vinylcyclohexene dioxide, glycidol, butadiene oxide, glycidyl methacrylate, diglycidyl ether of bisphenol A, 3,4-epoxycyclohexylmethyl 3,4-epoxycyclohexanecarboxylate, 3,4-epoxy-6-methylcyclohexylmethyl 3,4-epoxy-6-methylcyclohexanecarboxylate, bis(3,4-epoxy-6-methylcyclohexylmethyl)adipate, dipentene oxide, epoxidized polybutadiene, 1,4-butanediol diglycidyl ether, polyglycidyl ether of phenolformaldehyde resole or novolak resin, resorcinol diglycidyl ether, and epoxy silicones, e.g., dimethylsiloxanes having cycloaliphatic epoxide or glycidyl ether groups. A wide variety of commercial epoxy resins is available and listed in "Handbook of Epoxy Resins" by Lee and Neville, McGraw-Hill Book Company, New York (1967) and in "Epoxy Resin Technology" by P. F. Bruins, John Wiley & Sons, New York (1968). Representative of the 1,3- and 1,4-cyclic ethers which can be polymerized in accordance with this invention are oxetane, 3,3-bis(chloromethyl)oxetane, and tetrahydrofuran.

Another useful class of cationically-sensitive monomers which can be polymerized in accordance with this invention is represented by the general formula $CH_2=C(Y)XR'$, where X is —O— or —NR''— (where R'' is hydrogen or lower alkyl), R' is hydrocarbyl, hydrocarbylcarbonyl, halohydrocarbyl, or hydroxyhydrocarbyl when X is oxygen, or R' is hydrocarbyl, hydrocarbylcarbonyl, or hydrocarbylsulfonyl when X is nitrogen, and Y is hydrogen, alkyl, aryl, or other hydrocarbyl, or R' (as hydrocarbylcarbonyl) and R'' can be connected to form a 5- or 6-membered cyclic structure containing nitrogen as a hetero ring atom. The term "hydrocarbyl" is used herein in its usual sense to mean alkyl, alkenyl, aryl, cycloalkyl, cycloalkenyl, alkaryl, arylalkyl, and the like. In general, monomers of this type contain a vinyl group and are typified by vinyl alkyl ethers, such as vinyl methyl ether, vinyl ethyl ether, vinyl n-butyl ether, vinyl 2-chloroethyl ether, vinyl isobutyl ether, vinyl phenyl ether and vinyl 2-ethylhexyl ether, vinyl ethers of substituted aliphatic alcohols such as divinyl ether of butanediol, hydroxybutyl vinyl ether, and N-vinyl compounds such as N-vinyl-N-methyl octanesulfonamide and N-vinylpyrrolidone. A description of vinyl monomers and their use in preparing polymers is set forth in "Vinyl and Related Polymers," by Schildknecht, published by John Wiley & Sons, Inc., New York (1952).

Other cationically-sensitive monomers which can be polymerized in this invention include ethylenically unsaturated hydrocarbon such as isobutylene, 1,3-butadiene, isoprene, styrene, and divinylbenzene, especially the vinyl benzenes, cyclic formals such as trioxane, 1,3-dioxolane, 2-vinyl-1,3-dioxolane and methyl-1,3-dioxolane, and cyclic siloxanes which can contain various groups attached to the silicon atom such as a hydrocarbon radical (alkyl, aryl, alkaryl), an alkenyl hydrocarbon radical (vinyl, allyl or acryloyloxyalkyl), a halogenated hydrocarbon radical, a carboxy-containing hydrocarbon radical or ester group, a cyanohydrocarbon radical, hydrogen, halogen or a hydroxy group. Representative cyclic siloxanes are hexamethylcyclotrisiloxane, octamethylcyclotetrasiloxane, phenylheptamethylcyclotetrasiloxane, vinylheptamethylcyclotetrasiloxane, methacryloyloxymethylheptamethylcyclotetrasiloxane, bromomethylheptamethylcyclotetrasiloxane, 3-chloropropylheptamethylcyclotetrasiloxane, 1,2,3-tris(3,3,3-trifluoropropyl)-1,2,3-trimethylcyclotrisiloxane, acetoxymethylheptamethylcyclotetrasiloxane, cyanomethylheptamethylcyclotetrasiloxane, 1,2,3-trihydro-,1,2,3-trimethylcyclotrisiloxane, and chloroheptamethylcyclotetrasiloxane. Other known cyclic siloxanes are listed in "Chemistry and Technology of Silicones" by Walter Noll, Academic Press, New York (1968), Tables 41, 44 and 45.

The cyclic siloxanes can also be polymerized in the presence of relatively low molecular weight linear siloxanes such as hexamethyldisiloxane, chloropentamethyldisiloxane and octamethyltrisiloxane which serve to terminate the growing chain and provide stable fluids or fluids having reactive end groups.

There is a host of commercially available cationically-sensitive monomers which can be used in this invention. In particular, cyclic ethers which are readily available include propylene oxide, oxetane, epichlorohydrin, tetrahydrofuran, styrene oxide, vinyl-cyclohexene oxide, glycidol, glycidyl methacrylate, octylene oxide, phenyl glycidyl ether, 1,2-butane oxide, diglycidyl ether of bisphenol A (e.g., "Epon 828" and "DER 331"), vinylcyclohexene dioxide (e.g., "ERL-4206"), 3,4-epoxycyclohexylmethyl-3,4-epoxycyclohexanecarboxylate (e.g., "ERL-4221"), 3,4-epoxy-6-methylcyclohexylmethyl-3,4-epoxy-6-methylcyclohexanecarboxylate (e.g., "ERL-4201"), bis(3,4-epoxy-6-methylcyclohexylmethyl)adipate (e.g., "ERL-4289"), aliphatic epoxy modified with polypropylene glycol (e.g., "ERL-4050" and "ERL-4052"), dipentene dioxide (e.g., "ERL-4269"), epoxidized polybutadiene (e.g., "Oxiron 2001"), silicone epoxy (e.g., "Syl-Kem 90"), 1,4-butanediol diglycidyl ether (e.g., "Araldite RD-2"), polyglycidyl ether of phenolformaldehyde novolak (e.g., "DEN-431," "Epi-Rez 521" and "DEN-438"), resorcinol diglycidyl ether (e.g., "Kopoxite"), polyglycol diepoxide (e.g., "DER 736"), polyacrylate epoxide (e.g., "Epocryl U-14"), urethane modified epoxide (e.g., "QX3599"), polyfunctional flexible epoxides (e.g., "Flexibilizer 151"), and mixtures thereof as well as mixtures thereof with co-curatives, curing agents, or hardeners which also are well known (see Lee and Neville and Bruins, supra). Representative of the co-curatives or hardeners which can be used are acid anhydrides such as nadic methyl anhydride, cyclopentanetetracarboxylic dianhydride, pyromellitic anhydride, cis-1,2-cyclohexanedicarboxylic anhydride, and mixtures thereof.

In general, the polymerization of cationically-sensitive monomers with the cyclic anhydrides of this invention can be carried out at room temperature for the majority of cationically-sensitive monomers, although low temperature (e.g., $-10°$ C.) or elevated temperatures (e.g., 30° to 200° C., preferably 50° to 100° C.), can be used to either subdue the exotherm of polymerization or to accelerate the polymerization. In the case of latent amide catalysts of this invention, temperatures generally in the range of 50° to 250° C., preferably from 80° to 150° C., can be used. The temperature of polymerization and amount of catalyst will vary and be dependent on the particular cationically-sensitive monomer used and the desired application of the polymerized or cured product.

The amount of cyclic anhydride or amide derivative thereof to be used as a catalyst in this invention (i.e., a catalytically effective amount) should be sufficient to effect polymerization of the cationically-sensitive monomer under the desired use conditions. Such amount generally will be in the range of about 0.01 to 20 weight percent, preferably 0.5 to 5 weight percent, and most preferably 1 to 2 weight percent, based on the weight of cationically-sensitive monomer.

Solvents can be used to assist in dissolution of the cyclic anhydride or amide derivative thereof in the cationically-sensitive monomer, and are preferred for use with amide derivatives. Representative solvents include acetone, methylene chloride, ethyl acetate, methyl ethyl ketone, acetonitrile, p-dioxane, and the dimethyl ether of ethylene glycol (glyme). In general, in compositions containing cyclic anhydride catalysts, basic solvents or basic impurities in the monomer are avoided to prevent deactivation of the anhydride catalyst.

The curable or polymerizable compositions of this invention, consisting of or consisting essentially of the cationically-sensitive monomer(s) and said cyclic anhydride or amide derivative thereof as catalyst, can be used for applications like those cationically-sensitive monomer systems cured with other catalysts, such as epoxides cured with $BF_3$ or the complex of $BF_3$ with diethyl ether. Also, curable compositions of the invention comprising cationically-sensitive monomer(s), said cyclic anhydride or amide derivative thereof as catalyst, and other adjuvants (e.g., fillers, reinfocements, pigments, extenders, plasticizers and surface modifying agents) can be prepared in the same manner as compositions containing cationically-sensitive monomers, other catalysts, and adjuvants. For example, the curable compositions of this invention can be used as adhesives, caulking and sealing compounds, casting and molding compounds, potting and encapsulating compounds, impregnating and coating compounds, etc., depending on the particular monomers and/or catalyst used. Where the catalyst is used in its latent form, the curable composition can be used as a one-component or cured-in-place system, such capability enhancing its use for the applications mentioned above. One particular application where such capability can be employed is in the electrical arts, where such latently curable compositions can be used to coat or impregnate for insulation or protective purposes electrical motor windings or coils, transformers, capacitors, electrical terminals, cables, and other electrical devices.

The curable epoxy composition of this invention can be used to make shaped articles of self-supporting, structural, filled or reinforced epoxy resin composites, such as glass fiber cloth reinforced epoxy resin composites, useful, for example, as repair materials. The various fillers, reinforcements, and other particulate materials to be mixed or coated with or dispersed in the curable compositions of this invention to make the composites of this invention, as well as methods of processing these materials in making the composites, and their applications, are those known to the art. In this connection, reference is made to "Modern Composite Materials," edited by Brautman and Krock, published by Addison-Wesley Publishing Company, Reading, Mass. (1967); and "Handbook of Fiberglass and Advanced Plastics Composites," edited by G. Lubin, published by Van Nostrand Reinhold Company, New York, N.Y. (1969).

The objects and advantages of this invention are further illustrated by the following examples, but the particular materials and amounts thereof recited in these examples as well as other conditions and details should not be construed to unduly limit this invention.

EXAMPLE 1

This example shows a general procedure useful for the preparation of cyclic anhydrides of this invention.

To a stirred solution of 300 ml of methanol and 50 ml of water, cooled with an ice-water bath, was slowly added 50.2 g of 4-fluorosulfonylperfluorobutyryl fluoride. An aqueous base solution containing about 23 g of sodium hydroxide and 23 ml of water was then added with cooling. Additional aqueous base solution was added until the reaction mixture was neutral to pH paper. The reaction mixture was stirred for two hours and filtered to remove sodium fluoride. The filtrate was distilled to remove volatiles and the residue dried on a steam bath giving 51.3 g of the disodium salt of 4-sulfoperfluorobutyric acid, in the form of a white solid. About 20 g of the sodium salt was dissolved in water and ion-exchanged using "Amberlite IR-120" ion-exchange resin. The acidic aqueous solution was evaporated on a steam bath, yielding 16 g of the hydrate of 4-sulfoperfluorobutyric acid.

4-Sulfoperfluorobutyric acid (7.8 g, azoeotropically dried with toluene) was mixed in a flask under nitrogen with 15 g of phosphorus pentoxide. The flask was equipped for distillation under anhydrous conditions and heated with a sand bath to a temperature of 260° C., giving a distillate of 3.2 g of the cyclic anhydride of 4-sulfoperfluorobutyric acid, b.p. 76°-78° C. The identity of the anhydride was established by infrared, fluorine nuclear magnetic resonance (Fnmr), and mass spectral analyses. The anhydride is highly reactive, e.g., reacts with moist air, and is stored under anhydrous conditions.

EXAMPLE 2

In a 500 ml three-necked flask fitted with a mechanical stirrer, thermometer, condenser and addition funnel, and containing a cooled solution of 84.9 g (1.52 mol) of KOH dissolved in 84.9 g water, was added gradually over about 0.5 hour, at a rate so that the reaction temperature did not exceed about 35° C., 69.3 g (0.30 mol) of FO$_2$SCF$_2$CF$_2$COF (from the electrochemical fluorination of

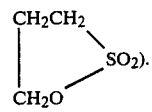

Stirring under ambient conditions was continued for about 0.5 hour. The temperature was next raised to about 100° C. and stirring continued under these conditions for four hours. The reaction mixture was cooled and the solid crystalline product filtered, rinsed with 50 ml cold water, and the crystals dried under reduced pressure. The yield of KO$_3$SCF$_2$CF$_2$COOK salt was 52 g.

Ten grams of KO$_3$SCF$_2$CF$_2$COOK were dissolved in 30 ml warm water and placed in a 50 cm×2.5 cm glass column containing a 20 cm bed of "Amberlite IR-120" ion-exchange resin in the acid (H+) form, which had been previously prepared by treating the column with 6N hydrochloric acid and rinsing with distilled water. The column was eluted with distilled water. The first 150 ml of eluate was concentrated under reduced pressure to yield the hydrate of 3-sulfoperfluoropropionic acid, HO$_3$SCF$_2$CF$_2$COOH.8H$_2$O.

To a stirred mixture of 30 g of phosphorus pentoxide in 50 ml of tris(perfluoroamyl)amine in a 250 ml, three-necked flask fitted with a thermometer, mechanical stirrer and anhydrous nitrogen gas inlet, and connected to a trap cooled to −78° C. with "Dry Ice", was added 5.0 g of HO$_3$SCF$_2$CF$_2$COOH.8H$_2$O.

The reaction mixture was heated over a 1.5 hour period to a maximum of 165° C. while stirring and purging with a slow stream of nitrogen gas. Warming the −78° C. trap gave 3.2 g of a colorless liquid, b.p. 54°-56° C. The infrared spectrum of the liquid was consistent with the structure:

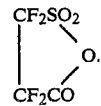

EXAMPLE 3

Using the method of Example 1, 50 g of a mixture containing about 75 mol percent 4-fluorosulfonylperfluorobutyryl fluoride and about 25 mol percent of a mixture of 3-fluorosulfonyl-2-trifluoromethylperfluoropropionyl fluoride and 3-fluorosulfonyl-3-trifluoromethylperfluoropropionyl fluoride was hydrolyzed with aqueous sodium hydroxide, giving 52.3 g of dry sodium salt mixture. The Fnmr spectrum indicated the presence of a mixture of about 75 mol % of the disodium salt of 4-sulfoperfluorobutyric acid and about 12 mol % each of the disodium salts of the isomeric acids 3-sulfo-2-trifluoromethylperfluoropropionic acid and 3-sulfo-3-trifluoromethylperfluoropropionic acid. The sodium salt mixture (20 g) was ion-exchanged giving 16 g of a mixture of the hydrates of the above sulfoperfluoroalkanecarboxylic acids.

Mixing of 8.3 g of the above acid hydrates and 17 g of phosphorus pentoxide in a flask followed by heating in a sand bath to a temperature of 250° C. gave 3.5 g of distillate (b.p., 70°-75° C.) which contained the cyclic anhydride of 4-sulfoperfluorobutyric acid as the major component along with about 10 mol % each of the cyclic anhydrides of 3-sulfo-2-trifluoromethylperfluoropropionic acid and 3-sulfo-3-trifluoromethylperfluoropropionic acid. The structures of these latter two anhydride compunds are:

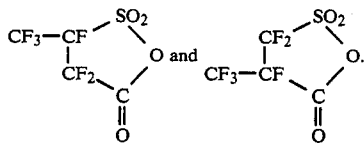

The next three examples show the preparation of amide derivatives of cyclic anhydrides of this invention.

EXAMPLE 4

Under anhydrous conditions, 1.9 g of the mixture of cyclic anhydrides of Example 3 was slowly added to a stirred solution of 1.9 g of diethylamine and 20 ml of diethyl ether in a 100 ml flask cooled with an ice-water bath. Formation of a lower phase, insoluble product occurred immediately. The mixture was stirred for 0.5 hour and the ether distilled off. The residue was heated with warm water under reduced pressure giving 2.8 g of an amber oily residue. Analyses of the oil by infrared and Fnmr indicated the presence of a mixture of

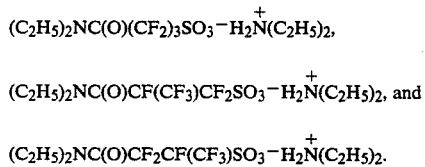

EXAMPLE 5

Using the method of Example 4, aniline (1.7 g) in 25 ml of diethyl ether was allowed to react with the anhydride of 4-sulfoperfluorobutyric acid (1.1 g), giving a white solid product. After stirring the mixture for 1 hr, 1.0 g of solid product was isolated by filtration. Analyses indicated high purity

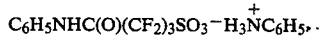

EXAMPLE 6

Under anhydrous conditions, 1.0 g of ammonia was slowly bubbled into a solution of the cyclic anhydride of 3-sulfoperfluoropropionic acid (Example 2, 1.0 g) which had been dissolved in acetonitrile. The resulting mixture was distilled under reduced pressure, giving 1.0 g of the ammonia reaction product which was a heavy grease soluble in acetone. Analyses by infrared and Fnmr indicated the presence of essentially a 1:1 mixture of

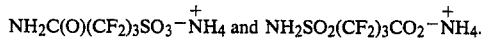

The next five examples show the use of cyclic anhydrides of this invention as catalysts for the polymerization of cationically-sensitive monomers.

EXAMPLE 7

The cyclic anhydride of 3-sulfoperfluoropropionic acid (0.04 g) was added under nitrogen to a glass vial containing 2.4 g of commercial tetrahydrofuran. The vial was capped and polymerization observed at room temperature. After about 20 hours a heavy grease was obtained. A portion of the polymer was stirred with water for four hours. Next, the insoluble polymer was removed and allowed to air dry. A high molecular weight, tough, leathery polymer of tetrahydrofuran was obtained.

EXAMPLE 8

Using the method of Example 7, 0.04 g of the cyclic anhydride of 3-sulfoperfluoropropionic acid was added to 2.0 g of styrene. An immediate, very exothermic polymerization resulted. After 2 hours at 25° C., the resulting polymer was a brown, essentially non-flowable, soft solid.

EXAMPLE 9

Using the method of Example 7, 0.05 g of the cyclic anhydride of 3-sulfoperfluoropropionic acid was added to 2.2 g of N-vinyl-2-pyrrolidinone. An immediate exothermic polymerization occurred and after five minutes at 25° C., the resulting polymer was an amber, heavy grease.

EXAMPLE 10

Using the method of Example 7, 0.04 g of the cyclic anhydride of 3-sulfoperfluoropropionic acid was added to 3.9 g of "ERL 4221" epoxy resin. Immediate gelation occurred and after four hours at 25° C., a solid polymer dispersed in the epoxy liquid was obtained.

EXAMPLE 11

Using the method of Example 7, 0.06 g of the cyclic anhydride of 3-sulfoperfluoropropionic acid was added to 3.3 g of octamethylcyclotetrasiloxane. After about three days at 25° C., a colorless, non-tacky gum characteristic of a very high molecular weight polydimethylsiloxane polymer was obtained.

The next two examples show the use of amide derivatives of cyclic anhydrides of this invention as latent catalysts for the polymerization of cationically-sensitive monomers.

EXAMPLE 12

To a glass vial was added 0.03 g of the ammonia reaction product of Example 6 and 2.0 g of "ERL 4221" epoxy resin. The mixture was heated at 50° C. for one minute giving a homogeneous yellow fluid. No evidence of polymerization was observed on storage of the fluid at room temperature for three days, indicating latency of the catalyst. The fluid was then heated at 125° C. for 15 minutes giving a brown, non-flowable solid polymer, having utility as a potting compound.

EXAMPLE 13

To a glass via containing a solution of 0.04 g of the aniline reaction product of Example 5 and about 0.06 g of acetone was added 1.2 g of "ERL 4221" epoxy resin. The vial was capped and the mixture heated at 50° C. for 1 minute giving a clear light yellow fluid. No evidence of polymerization was observed on storage of the fluid at room temperature for 20 hr, indicating latency of the catalyst. The fluid was then heated at about 125° C. for 5 min. giving a hard, solid polymer.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. Carboxamides and sulfonamides, useful as latent catalysts for the polymerization of cationically-sensitive monomers, prepared by a process comprising reacting at least one cyclic anhydride of an omega-sulfoperfluoroaliphaticcarboxylic acid, said cyclic anhydride having the formula:

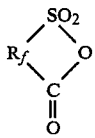

wherein $R_f$ is perfluoroalkylene having 2 to 5 catenary carbon atoms or perfluorocycloalkylene having 4 to 7 ring atoms, $R_f$ optionally being substituted by one or more straight chain, branched, or cyclic perfluoroalkyl groups of 1 to 12 carbon atoms, with $R_f$ having a total of up to 14 carbon atoms, with at least one protonic nitrogenous base having a $pk_b$ of less than about 13.2.

2. Carboxamides and sulfonamides, useful as latent catalysts for the polymerization of cationically-sensitive monomers, said carboxamides and sulfonamides having the formulae:

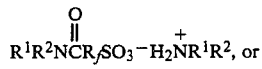

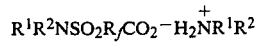

wherein $R_f$ is perfluoroalkylene having 2 to 5 catenary carbon atoms or perfluorocycloalkylene having 4 to 7 ring atoms, $R_f$ optionally being substituted by one or more straight chain, branched, or cyclic perfluoroalkyl groups of 1 to 12 carbon atoms, with $R_f$ having a total of up to 14 carbon atoms, and each $R^1$ and $R^2$ is independently hydrogen, or a monovalent organic radical which can be the same as or different from any other $R^1$ or $R^2$, or each $R^1$ and $R^2$ bonded to the same N atom can combine with one another to form a cyclic structure containing the N atom, and $R^1$ and $R^2$ contain from 1 to about 20 carbon atoms, can be straight chain, branched or cyclic, can be saturated, unsaturated or aromatic, can contain skeletal or catenary hetero atoms other than carbon, and can be unsubstituted or substituted with non-interfering moieties.

3. Carboxamides according to claim 2, having the formula

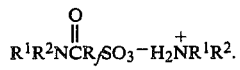

4. Sulfonamides according to claim 2, having the formula

* * * * *